(12) United States Patent
Berndt et al.

(10) Patent No.: US 12,210,004 B2
(45) Date of Patent: Jan. 28, 2025

(54) DATA ANALYSIS SYSTEM, MOBILE GAS MEASURING DEVICE AND DATA PROCESSING UNIT FOR SUCH A SYSTEM

(71) Applicant: Dräger Safety AG & Co. KGaA, Lübeck (DE)

(72) Inventors: Malte Berndt, Lübeck (DE); Christof Rodehorst, Lübeck (DE); Raphael Maas, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 423 days.

(21) Appl. No.: 17/683,700

(22) Filed: Mar. 1, 2022

(65) Prior Publication Data
US 2022/0283134 A1    Sep. 8, 2022

(30) Foreign Application Priority Data
Mar. 2, 2021 (DE) .................. 10 2021 105 015.4

(51) Int. Cl.
*G01N 33/00*    (2006.01)
*H04L 67/12*    (2022.01)

(52) U.S. Cl.
CPC ......... *G01N 33/0075* (2013.01); *H04L 67/12* (2013.01)

(58) Field of Classification Search
CPC  H04L 67/12; G01N 33/0075; G01N 33/0063; G01N 33/0067; G01N 33/0062; G01N 33/0031; G01N 33/0009; G01N 33/0006; G01N 33/0004; G01N 33/004; G01N 35/00871; G01N 2035/0091; G01N 21/3504; H04Q 2209/40; H04Q 2209/823; H04Q 2209/86; H04Q 2209/43; H04Q 2209/50; H04Q 2209/47; H04Q 2209/10; H04Q 9/00; G16H 40/63; G16H 40/67; G05B 23/0221; G05B 23/0283;
(Continued)

(56) References Cited

U.S. PATENT DOCUMENTS 11,709,819 B2 * 7/2023 Tirapu Azpiroz ..... G06N 5/022
702/22
2002/0198679 A1 * 12/2002 Victor ................ G05B 23/0264
702/176
(Continued)

FOREIGN PATENT DOCUMENTS

WO    WO-03091672 A1 * 11/2003 ......... G01F 23/0069

*Primary Examiner* — Jeffrey P Aiello
(74) *Attorney, Agent, or Firm* — McGlew and Tuttle, P.C.

(57) ABSTRACT

A data analysis system includes a gas measuring device (2), providing current data and/or historical data, which are stored in a memory (3), and a data processing unit (1). The data includes information on a gas measuring device time of data acquisition. The device transmits data to an interface configured to receive the data and to feed data to the data processing unit and/or to an additional memory (5). A data identification unit (6) is configured to add a specific identifier to the data and add a piece of information on a system time during the data transmission and/or the gas measuring device time during the data transmission. The data processing unit is configured to process the data provided by the gas measuring device and/or by the additional memory such that the system time and the gas measuring device time are taken into consideration.

18 Claims, 1 Drawing Sheet

(58) Field of Classification Search
CPC ....... G05B 23/024; G06F 17/18; G06F 18/25; G06F 18/21
USPC .......... 73/23.2, 861, 861.356, 40.7; 340/540, 340/539.26, 632, 691.6; 422/83; 700/108, 28, 83, 9, 110, 266, 1; 702/50, 702/188, 19, 182, 183, 189, 104, 62, 22, 702/179, 24, 85, 184, 187, 127, 23, 51, 1, 702/2, 27, 3, 25, 178, 116, 36; 703/11; 709/224, 218, 201

See application file for complete search history.

(56) References Cited

U.S. PATENT DOCUMENTS

| | | | |
|---|---|---|---|
| 2004/0075566 A1* | 4/2004 | Stepanik | G01N 33/0075 340/870.3 |
| 2008/0243393 A1* | 10/2008 | Yamamoto | A61B 5/02438 702/19 |
| 2011/0161885 A1* | 6/2011 | Gonia | G08B 21/12 715/764 |

* cited by examiner

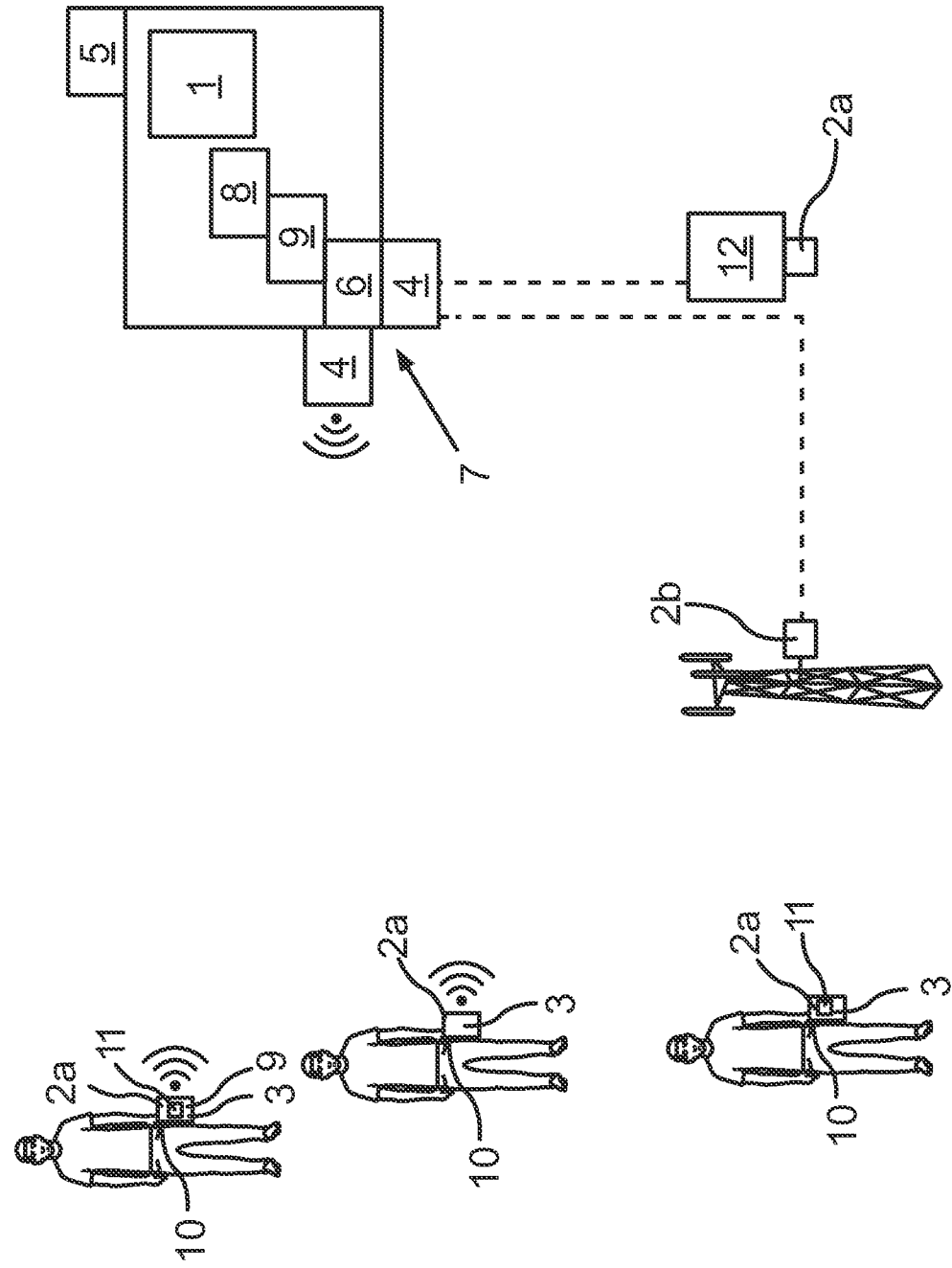

DATA ANALYSIS SYSTEM, MOBILE GAS MEASURING DEVICE AND DATA PROCESSING UNIT FOR SUCH A SYSTEM

CROSS REFERENCE TO RELATED APPLICATIONS

This application claims the benefit of priority under 35 U.S.C. § 119 of German Application 10 2021 105 015.4, filed Mar. 2, 2021, the entire contents of which are incorporated herein by reference.

TECHNICAL FIELD

The present invention pertains to a system for analyzing data as well as to a mobile gas measuring device and to a data processing unit for such a system. The system has at least one gas measuring device, which is set up to provide current and/or historical data, which are stored in a memory of the gas measuring device and contain information on at least one gas measuring device time at the time of detection of the historical data and to transmit them in a wired or wireless manner to an interface, which is configured to be able to receive the current and/or historical data and to be able to feed them to a data processing unit and/or to another memory. Further, a data identification unit is provided, which is configured to add a specific identifier at least from time to time to the data provided by the gas measuring device.

TECHNICAL BACKGROUND

Different systems, especially monitoring systems for industrial plants, such as refineries, chemical plants and mines, are known from the state of the art, which have mobile and stationary gas measuring devices, which detect concentrations of different gases in a measurement area and thus detect ambient parameters and generate alarm signals in case of inadmissible deviations. If a gas measuring device detects an overshooting of a limit value, this device carries out an alarm generation either itself or sends an alarm signal to a central data processing unit, which is often a part of a control room. Mobile or portable gas measuring devices for the personal protection of people are frequently used, which warn the device user by means of an alarm signal if toxic gases or vapors assume a hazardous concentration in the immediate area surrounding the device user, if a combustible or explosive gas mixture is present or if there is a deficiency or inadmissible excess of oxygen.

The prior-art mobile gas measuring devices usually have internal memories, so-called data loggers, in which both detected measured values and defined events, e.g., errors or alarms that have occurred, are stored. These data stored on the device may be used to perform a subsequent analysis of the situation with these data in case of the occurrence of alarms or in case of an incident.

Meanwhile, mobile gas measuring devices which transmit generated data in a wireless manner to a central data processing unit or to a central memory have been increasingly used. It is thus possible to transmit the detected measured values and information on alarms or errors that have occurred during the measurement time period either in real time or at least as soon as a data connection is present and thus to make them available comparatively rapidly for further processing, for example, in a control room of an industrial plant.

If already existing monitoring systems are retrofitted with such gas measuring devices, which transmit measured data or other information in a wireless manner, the problem often arises that different types of mobile gas measuring devices, namely, devices that can transmit data in a wireless manner, on the one hand, and, on the other hand, devices that must be coupled with a read-out device in order for the data being stored on these devices to be able to be transmitted are used side by side. If data are transmitted in this case from the different devices to a central memory or to a central data processing unit, both historical data and current data are available to the system. A comparatively large amount of data generated at different times is thus available, so that it must be ensured during a data processing that the historical data and the current data are put into a correct chronological relationship with one another and that taking individual data sets into consideration multiple times is avoided.

SUMMARY

Based on the solutions known from the state of the art for the analysis of data that are generated by means of mobile and/or stationary gas measuring devices and are fed to a central data processing unit for analysis, as well as based on the problems described above, a basic object of the present invention is to provide an improved system for the analysis of data, especially to perfect a system for the analysis of data that are detected and provided by mobile and/or stationary gas measuring devices such that both historical data and current data, especially data transmitted in real time, are taken into consideration and are available for a reliable data analysis. By using data generated at different times, above all historical and current data, which were detected or generated by a mobile gas measuring device, it shall be possible to carry out analyses that are based on a comparatively large amount of data and thus make possible the analysis of hazardous situations and risk potentials with a high accuracy and spatial resolution. It is desirable for this purpose that historical and current data shall be able to be correlated with one another. In particular, the accuracy of analyses shall thus be increased and a broader spatial coverage shall be achieved during the monitoring of a production site and a more complete picture of the situation shall be provided. It is, furthermore, important in this connection that the data generated be available as rapidly as possible and in an orderly manner in order to guarantee a rapid, accurate and reliable data analysis.

It is, furthermore, especially significant for accurate analyses to avoid taking into consideration identical data sets multiple times and to put historical and current data into a correct chronological order in terms of the time at which they were detected and transmitted during their storage or processing.

Furthermore, effective utilization of the large storage capacities of central memories of so called cloud solutions should be made possible by means of the technical solution to be proposed and, furthermore, it should be possible to minimize and/or specifically set or divide the time period needed for a data transmission.

The above-described object is accomplished with a system as disclosed herein, with a mobile gas measuring device as disclosed herein and with a data processing unit, which has features as disclosed herein. Advantageous embodiments of the present invention will be explained in more detail in the following description partially with reference to the FIGURES.

The present invention pertains to a system for analyzing data with at least one gas measuring device, which is set up to provide current data and/or historical data, which are stored in a memory of the gas measuring device and contain information on a gas measuring device time at the time of the detection of the historical data, and to transmit them in a wired or wireless manner to an interface, which is configured to receive the current data and/or the historical data and to feed them to a data processing unit and/or to another memory, and with a data identification unit, which is configured to add a specific identifier at least from time to time to the data provided by the gas measuring device. The system has been perfected according to the present invention such that the data identification unit is set up to add information on a system time during the data transmission and the gas measuring device time during the data transmission to the data provided by the gas measuring device and that a processing of the data provided by the gas measuring device and/or by the additional memory is carried out such that the system time and the gas measuring device time are taken into consideration.

It is thus possible by means of the above-described system for the analysis of data to use both historical data and current data, which are provided by a gas measuring device, especially by a mobile or portable gas measuring device. Information in reference to at least one gas concentration detected by a gas measuring device, errors that occurred during the operation and/or alarms generated during the operation are preferably transmitted in this case and are made available for a further data processing and data analysis. The data are provided in this case in a such a form that a multiple use of identical data and/or the taking into consideration of incorrect detection times do not occur, regardless of whether only current data, only historical data or simultaneously historical and current data are transmitted at least from time to time. It is ensured by the provision of a time stamp, which preferably contains information on the device time at the time of the data acquisition and/or data transmission, on the one hand, and by a synchronization of the detection times with a system time, on the other hand, that all the data present in the system are synchronized with a uniform time. It is thus guaranteed that both historical and current data are taken into consideration in the order in which they were generated and/or are assigned correctly to events or errors that occurred at a defined time.

It is, furthermore, possible according to the present invention to use both mobile or portable gas measuring devices, which are set up for a wireless data transmission, and those whose internal memory is read out only from time to time, in one system together with stationary gas measuring devices, which do, in turn, transmit data to a central data processing unit in a wireless and/or wired manner. The system for the analysis of data, which is configured according to the present invention, is set up such that a reliable distinction is always made between data that have already been transmitted to a central data processing unit and/or to a central memory, for example, via a wireless interface, and data that have yet to be transmitted, e.g., historical data, which were generated already at an earlier time and are being stored on the internal memory of a mobile gas measuring device and are transmitted to the data processing unit only after connection to a special transmission unit.

The data identification unit, which is set up to add information on the gas measuring device time as well as the system time at the time of the data transmission to the data transmitted from the gas measuring device, may be configured as a separate component or else be an integral part of another component of the system according to the present invention. The data identification unit may be a part of a gas measuring device, of the central data processing unit, of an interface and/or of another system component intended for the data transmission or data processing.

The interface and/or the data identification unit are integrated into a gateway according to a special embodiment of the present invention. A gateway is defined according to the description as an element for data transmission, via which a connection can be established between two systems or between a system and a subsystem. It is advantageous, in this connection, that data sent through the gateway are processed in the gateway, especially supplemented (enriched) with at least one additional piece of information. According to a special variant, provisions are made for the interface to be set up to transmit information to the gas measuring device when a data connection is established between the gas measuring device and the interface via the connection established. The gas measuring device is preferably configured in this case such that the information is stored in the memory of the gas measuring device via the connection established. Furthermore, it is advantageous that when the data connection between the gas measuring device and the interface is severed, information on the severing carried out is generated in the gas measuring device and is likewise stored in the memory of the gas measuring device. It is preferable, on the one hand, to assign the respective information on the performed establishment of the connection to the first data set then transmitted or to the last data set not transmitted and, on the other hand, to assign the severing of the connection to the data set transmitted last or to the first data set no longer transmitted during the just concluded transmission interval. According to this special embodiment, the information on whether a data transmission connection to the central data processing unit is present and on whether this connection still exists or was already ended is thus always present in the memory of a gas measuring device. As soon as the data transmission connection between the gas measuring device and the central data processing unit is again actively severed or the connection becomes broken, this time is noted in system time or in gas measuring device time. It is thus ensured that the data generated between the two inputs of the times, which data were thus generated while a data transmission connection was established, are not transmitted again to the central data processing unit or at least are not taken into consideration by this central data processing unit for a further processing and analysis.

According to a special variant of the present invention, a compensation unit is provided, which is set up to convert the time at which the historical data are detected and/or the time at which the historical data are transmitted and/or the time at which the current data are transmitted, which detection time is present in gas measuring device time, into the corresponding time in gas measuring device time, taking into consideration the system time. The system time is preferably added at the time of the detection and/or transmission to the respective transmitted data set. Different time zones or time systems, which may be present in such an interlinked monitoring system, are taken into consideration in such a technical solution. As soon as the gas measuring device time ceases to agree with the system time, the respective transmitted data are complemented by the information of the system time at the detection time and/or transmission time or the data component for the gas measuring device time is overwritten with the correct system time. In this connection, all the data transmitted to the central data processing unit may be provided with a time stamp, which indicates the transmission time in system time. It order to make it always possible to supplement the data with the information on the correct system time, the compensation unit is preferably synchronized with the system time.

The detection times of the data, which are related to the gas measuring device time, are compensated for historical data, which are already present in the system and/or are transmitted from a gas measuring device to the central data processing unit, in a special embodiment of the present invention. Both the gas measuring device time is read from a gas measuring device and the current system time is determined for this purpose at the time of a data transmission, and these two pieces of time information are added to the read-out data set and are transmitted together with this to the central data processing unit. It is then possible based on the current gas measuring device time as well as on the current system time to subsequently convert the detection times of the transmitted data from the gas measuring device time into the system time.

According to another embodiment of the system according to the present invention, a compression unit is provided, which forwards the data detected by a gas measuring device and/or made available via the interface as a function of at least one decision criterion to the data processing unit and/or to the additional memory. The compression unit is advantageously configured such that data are deleted if the decision criterion is met at least to a certain degree. As an alternative or in addition, the transmitted data may be compressed, preferably by parts of data sets being deleted, as a function of the decision criterion or the degree to which the decision criterion is met.

It is advantageous if the decision criterion is set on the basis of a change in a measured value, which takes place during a time interval, of an intensity of a measured value change and/or of a number of data detected within a time period. The decision criterion is thus preferably selected as a function of the data made available in order not to transmit or not to take into consideration either data that have little additional information content compared to already transmitted data or else in order to select especially relevant data, i.e., data with an especially important information content, from a group of data and to transmit them to the central data processing unit or to a memory.

In another special embodiment, the gas measuring device is configured as a mobile gas measuring device and it has at least one fastening element, which makes it possible to fasten and to detach the gas measuring device to/from a belt, a pocket, a piece of clothing, protective gear and/or a helmet without a tool. Furthermore, such a fastening element may be configured as a wristband, belt, waist belt, shoulder strap or neck-band, which makes it possible to fasten the gas measuring device over the clothing being worn by the measuring device user.

According to a special embodiment of the present invention the memory of the gas measuring device may have at least two memory areas, in which data, which contain specific information each, are stored. The gas measuring device, especially a mobile or portable gas measuring device, is preferably configured such that the data stored in the at least two memory areas are transmitted separately from one another. The data stored in the different memory areas may differ in respect to the manner in which the data were generated, the origin, the information content and/or the data size. It is especially preferable that measured data are stored in a first memory area of the memory of a gas measuring device, while errors that occurred during the operation of the gas measuring device, generated alarms or other pieces of information related to the operation or the service of the device are stored in at least one other memory area. Due to the provision of at least two memory areas, different data in reference to the data transmission may be prioritized in different manners and thus to read, e.g., certain data, e.g., information on events, alarms and/or measured data, regularly and at short time intervals, whereas other data, for example, forces, which have acted on the gas measuring device during the operation, are read at defined times only, for example, during a maintenance or a calibration.

Also, at least two interfaces are advantageously provided, and the gas measuring device is configured such that one of the at least two interfaces is selected for the data transmission as a function of a necessary transmission power and/or signal quality. The gas measuring device preferably has at least two transmission units in this case, so that the pairing necessary for a data transmission, comprising a transmission unit and an interface between the gas measuring device and the data processing unit, can be established. It is ensured with such a technical solution that the interface necessary for a reliable data transmission, which nevertheless requires as little energy as possible, is always selected and used as needed. The provision of different interfaces makes possible, moreover, an especially flexible operation and reliable operation of a gas measuring device, especially of a mobile or portable gas measuring device, in the monitoring of industrial production sites with a data analysis system configured according to the present invention.

The present invention also pertains, in addition to a data analysis system, to a mobile gas measuring device for use in a system that is configured according to at least one of the above-described embodiments.

In a special embodiment, the mobile gas measuring device has at least one memory. The generated data are stored in a rolling manner (on a rolling basis) in the memory, so that as soon as no more storage space is available, the oldest data in the memory are overwritten with the data just generated.

The memory preferably has at least two memory areas, which can be connected separately or together to the interface for transmitting data to the data processing unit. The establishment of a connection to the interface and hence indirectly to the data processing unit is initiated by a control unit of the mobile gas measuring device. According to a special variant of the of the present invention, the connection to the interface is established by the control unit on the basis of a decision criterion. It is possible by means of the decision criterion, which can be set by the user as needed, to establish a connection to the interface and/or to select the memory area of the memory, which memory area is to be taken into consideration, as a function of certain events, for example, the magnitude of measured values, of the information content of the generated data and/or of a distance between two consecutively detected measured values.

The present invention likewise pertains to a data processing unit for a system configured according to the present invention, which system is configured according to one of the above-described embodiments, and which is set up to detect a concentration of at least one gas and/or to generate at least one piece of information on errors, alarms and/or forces having acted on the gas measuring device, which errors, alarms and/or forces occurred during a past time interval, and to output this concentration and/or information via an output unit.

The present invention will be explained in more detail below without limitation of the general inventive idea on the basis of exemplary embodiments with reference to the FIGURES. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view showing a data analysis system configured according to the present invention.

DESCRIPTION OF PREFERRED EMBODIMENTS

Referring to the drawings, FIG. 1 shows in a schematic circuit diagram a data analysis system configured according to the present invention as it is used for monitoring an industrial production site and of different work areas thereof for the presence of inadmissible concentrations of selected gases or gas mixtures. The data are provided by a variety of gas measuring devices 2a, 2b, which are mounted partly stationarily at different points of the production site, e.g., of a refinery, another plant for producing chemicals or in a mine and are partly carried along by people working at the production site for their safety. The gas measuring devices 2a and 2b shown in FIG. 1 are thus both stationary gas measuring devices 2b and mobile or portable gas measuring devices 2a, which can be attached to the protective clothing or to the body of the device user by means of suitable fastening elements 10.

While the portable gas measuring devices 2a can be used in a flexible manner and are used above all for the protection of the particular gas measuring device user, the stationary gas measuring devices 2b continually detect the concentration of selected vapors, gases or gas mixtures in an area of the production site in order to ensure that no hazardous vapor or gas concentrations occur in the respective measurement areas and the plants arranged in this area are operated in a trouble-free manner.

Depending on the installation site and the fastening of the gas measuring device 2b, the stationary gas measuring devices 2b transmit the generated measured data as well as data that contain information concerning the occurrence of alarms or device errors during the measurement time period at first either in a wired or wireless manner to an interface 4 and from this to a central data processing unit 1, which is connected to a central memory 5 as an intermediate memory and/or as an storage memory. In this connection, the data transmitted via the interface 4 may be processed immediately after the data transmission, may be transmitted in the already processed or yet unprocessed form to another data processing unit and/or are stored at first in the central memory 5.

According to the exemplary embodiment being described here, the central data processing unit 1 is a part of a control room, from which the production site, especially the different production plants, are monitored and controlled as needed.

The portable gas measuring devices 2a used in the data analysis system according to FIG. 1 can be divided into two classes. On the one hand, there are gas measuring devices 2a that are not able to establish a wireless data transmission connection to the central data processing unit 1. These gas measuring devices 2a generate an alarm for the device user via an output unit 11, e.g., a display element or a speaker, doing so directly upon the detection of an overshooting of a limit (threshold) value for a permissible gas concentration or of an undershooting of a necessary oxygen concentration; the portable gas measuring devices 2a store the measured data generated as well as possibly generated data, which contain information on device errors and/or alarms that occurred during the measurement time period, but they do so at first only in an internal memory 3, a so-called data logger. The reading out of the internal memory 3, i.e., the transmission of the data being stored in this memory to the interface 4 usually takes place by means of an often stationarily operated read-out device 12, to which the mobile gas measuring device 2a is connected from time to time, for example, by insertion into a device shell with contacts. The reading out of the stored data frequently takes place during the charging of the battery, the calibration of the internal sensors of the device 2a or during other maintenance, cleaning or repair of the gas measuring device 2a. In this case the gas measuring device is configured to transmit the data in a wired or wireless manner to an interface either with a suitable interface 4 being integrated into the read-out device 12 or the read-out device 12 being connected in a wireless or wired manner to the interface 4, so that the data read from the memory 3 of the gas measuring device 2a can be transmitted via the interface 4 to the central data processing unit 1.

The generation of the data is thus carried out with a time difference before the data transmission, so that the data provided in this manner for the data processing unit 1 are called historical data.

The second class of mobile gas measuring devices 2a used according to the embodiment being described here is that of devices which have been increasingly used include or are associated with a wireless transmission means which establishes a wireless connection to a suitable interface 4 at least in certain areas of the production site, so that the generated data, especially measured data, are transmitted as current data in real time to the central data processing unit 1.

In this connection such mobile gas measuring devices 2a may be connected to the interface 4 for the transmission of data to the central data processing unit 1 during the entire time during which a device user is moving at the production site, or else that a data transmission connection is either present as a function of the network coverage in certain areas of the production site only or else it is established in a specific manner in selected areas only.

The mobile or portable gas measuring devices 2a are, in turn, configured such that, on the one hand, measured data and data that contain information on device errors or alarms that occurred during the measurement time period and contain information on the location of the gas measuring device 2a are transmitted to the central data processing unit 1 via the interface 4 and, on the other hand, an alarm signal is outputted via an output unit 11, e.g., a display element or a speaker, to the device user upon detection of an inadmissible limit value violation. Such an alarm signal is outputted in the form of an alarm sound, of a display on a display unit and/or as a vibration alarm. Additionally, an additional threshold value may be stored in the portable gas measuring device 2a, this threshold value being such that a pre-alarm, which preferably has at least one different property than the main alarm, is triggered when this threshold value is violated still before the limit value is reached.

Information on the location of the gas measuring device 2a can be generated and added to the transmitted data in this case in different manners, e.g., in an automated manner by means of a gateway, via which data generated by the gas measuring device 2a are transmitted; by manual input; by scanning an RFID tag or by analysis of a GPS signal. Likewise, an additional system component, which has a piece of information on the location of the gas measuring device 2a, may complement the transmitted data by a piece of location information or even that location information is determined on the basis of known motion information and is added to the transmitted data.

Thus, both stationary and mobile or portable gas measuring devices 2b, 2a are used in the system shown in FIG. 1, and the mobile gas measuring devices 2a transmit partly historical data and partly current data via the interface 4 to the data processing unit 1. The composition of the gas measuring devices that are located in the plant may, of course, change at any time. It must be possible for this reason at any time, regardless of the type of the data provided, i.e., regardless of whether the data are historical data or current data, to distinguish the data unambiguously and to put the times of their generation in the correct chronological relationship. It is consequently essential that it be ensured in the data analysis system being described here regardless of whether the data are historical data or current data, the time at which they were generated and the correct chronological sequence of the generation times be taken into consideration during the data processing. The data provided by the different gas measuring devices 2a, 2b must therefore be processed such that their information content will not be lost and the correct chronological order of their generation can be taken into consideration.

According to the embodiment shown in FIG. 1, this object is accomplished by at least one interface 4 being provided, which transmits a message to the gas measuring device 2a, 2b connected to the interface with the information that the gas measuring device 2a, 2b in question is connected now to the interface 4 and with the point in time starting from which a transmission of data to the central data processing unit takes place. The information on the establishment of the connection is, moreover, stored as an identifier in the memory 3 of the gas measuring device. If historical data have already been stored in this memory 3, these are identified such that the point in time starting from which historical data are read out from the memory 3 of the gas measuring device 2a, 2b is clearly known. As soon as the connection between the interface 4 and the gas measuring device 2a, 2b is severed again, regardless of whether this happens intentionally or unintentionally, the gas measuring device 2a, 2b generates an additional entry in the memory 3 of the gas measuring device 2a, 2b, which contains information on the termination of the connection especially based on the time of the termination. An unambiguous ID is preferably added to each entry, so that it can always be distinguished whether the data are already present, and the ID may be a time stamp or a counter. On the one hand, the information on the time of severing or establishment of a connection for the data transmission may be contained in this manner in the data, and, on the other hand, double entries are avoided.

If a connection is established thereafter between the interface 4 and the gas measuring device 2a, 2b, especially a mobile or portable gas measuring device 2a, it is ensured in this manner that the data that were stored between the two identifiers in the memory 3 of the gas measuring device 2a, 2b will not be transmitted once again to the data processing unit 1 and they will not be taken into consideration by this for the further processing.

Furthermore, the data analysis system shown schematically in FIG. 1 is configured such that the different times used by the gas measuring device 2a, 2b are taken into consideration, and the different times are synchronized with a uniform system time. According to the embodiment shown in FIG. 1, the interface 4 and a data identification unit 6 are for this purpose a part of a gateway 7, which at first supplements the data with a piece of information on the system time, i.e., it adds a so-called time stamp. In order to ensure that a uniform system time is used all the time, the gateway 7 is synchronized with an existing system time. A gas measuring device 2a, 2b likewise adds an identifier during a data transmission, which contains information on the gas measuring device time at this time to the transmitted data.

If historical data are now read out from gas measuring devices 1, especially from mobile gas measuring devices 2a, and are transmitted to the central data processing unit 1, the detection times are converted from the gas measuring device time into the system time by means of a compensation unit 8, which may be integrated into the central data processing unit 1. The processing, analysis and/or the analysis of the transmitted data consequently always take place on the basis of the system time, and this is true regardless of whether the data are current or historical data and whether the respective gas measuring device times are identical to the system time.

It is essential for the system described that a large quantity of data, namely, both historical and current data, are provided for a central data processing and are processed and analyzed there. Based on the large quantity of data, which are available for analyses, statements can be made about existing risks and/or on events that have occurred, for example, leaks or accidents, with a high accuracy and high spatial resolution. However, it should be taken into consideration in this connection that considerable quantities of data must at times be transmitted, stored and/or processed in the system described. It is useful for this purpose to reduce the quantity of the transmitted data to the extent that only the data that are really relevant for the later processing and analysis are transmitted and used later. The gas measuring devices 2a, 2b, especially the mobile gas measuring devices 2a, are configured in this connection such that only defined measured data are stored in the memory 3 of a gas measuring device 2a, 2b and/or are transmitted to the interface 4.

A measured value is preferably only stored and/or transmitted if a decision criterion stored in a control device of the gas measuring device 2a, 2b is met or not met at least to a degree that can be set. It is advantageously taken into consideration, among other things, by the decision criterion in this connection whether a data connection is present to a central data processing unit and/or to a central memory. Storage and/or transmission of data takes place, for example, only when a measured value is above or below a limit value, when there is a defined time interval between two measurements, when a mobile gas measuring device 2a has been moved over a defined distance and/or when there is a set distance between two measured values recorded consecutively. It is possible in this manner by the use of a compression unit 9, taking at least one decision criterion into consideration, to limit a storage and/or transmission of data and/or to delete already stored or transmitted data at least partially in order at least partially to compress the data set in this manner. The setting of the at least one decision criterion, which will be used as the basis for reducing the data that are stored, transmitted and/or processed, can be adapted to the respective operating conditions, especially to the hazard potential, which exists for a gas measuring device user.

Likewise, the properties of the sensors as well as of the measuring methods which are used in a gas measuring device may be taken into consideration. For example, what is significant is not always the deviation of a measured value in relation to a zero point, but, as, e.g., in the case of the oxygen content of 20.9 vol. % in the air, the deviation from a specific value.

Furthermore, the memories 3 of the gas measuring devices 2a, 2b are configured such that at least two different memory areas are provided, in which respective data with different information contents are stored. In this case as well information on alarms, error messages or other events may be stored in separate memory areas intended specifically for these purposes. Due to the provision of memory areas thus separated and of a suitably configured actuation of the memories 3, it is even possible to read out the memories 3 of the gas measuring devices 2a, 2b adaptively and thus to carry out the transmission of data to the interface 4 at defined times and/or to limit it to defined time periods or events. Thus, for example, larger memory areas or memory areas in which less safety-relevant data are being stored at comparatively long time intervals or in case of certain events may be read out only, e.g., at the time of a maintenance or calibration of a gas measuring device 2a, 2b, whereas smaller memory areas or memory areas containing especially safety-relevant information, e.g., measured values close to a limit value or alarm events, are read out more frequently.

The essential advantage of the data analysis system according to the present invention is that historical as well as current data are available for a data analysis with suitably configured gas measuring devices 2a, 2b and both with at least one correspondingly set-up interface 4 and a data processing unit 1. Based on the system described, it is possible to make available safety-relevant information on the gas concentrations prevailing at a production site and ambient parameters with high accuracy, high spatial resolution and over a comparatively large area. The prevailing overall situation can thus be assessed better and, in particular, a reliable risk assessment can be carried out. The measured concentration of selected gases, the number of alarms that occurred during a measurement period as well the clustering of defined errors are taken into consideration in this connection.

Because of the large quantity of data available, a thorough data analysis is made possible, from which properties and/or the changes in the properties of a gas measuring device 2a, 2b, which may be due to the fact that gas was admitted to the sensors being used, to environmental conditions prevailing during the measurements and to the age of the sensors, can be inferred with a high probability.

A comparatively large quantity of data can be analyzed precisely due to the suitable identification of the historical and current data generated and provided by the different gas measuring devices 2a, 2b. It is ensured here by means of the system according to the present invention that a double analysis of data is not carried out, partly because identifications are made in relation to the start and the end of a data transmission or the establishment and the severing of a data connection in the memories 3 of the gas measuring devices 2a, 2b and, moreover, unambiguous time stamps are added to the respective transmitted data, so that all the data used in a data processing unit 1 are synchronized with the system time. Likewise, an unambiguous ID can be added to the data in order to make it always possible to unambiguously identify the data.

While specific embodiments of the invention have been shown and described in detail to illustrate the application of the principles of the invention, it will be understood that the invention may be embodied otherwise without departing from such principles.

LIST OF REFERENCE NUMBERS

1 Data processing unit
2a Mobile gas measuring device
2b Stationary gas measuring device
3 Memory in the gas measuring device
4 Interface
5 Central memory
6 Data identification unit
7 Gateway
8 Compensation unit
9 Compression unit
10 Fastening element
11 Output unit
12 Read-out device

What is claimed is:

1. A system for analyzing data, the system comprising:
a gas measuring device configured to provide current data and/or historical data which are stored in a memory of the gas measuring device and contain information on the gas measuring device time at the time of a detection of the data, and to wire transmit or wirelessly transmit the data;
a data processing unit;
an interface configured to receive the current and/or historical data from the gas measuring device and to feed the received data to the data processing unit or to a central memory; and
a data identification unit, associated with the data processing unit and/or the central memory, and configured to add a specific identifier to the data provided by the gas measuring device, the data identification unit being further configured to add, to the data provided by the gas measuring device, information on a system time during the data transmission and information on a gas measuring device time during the data transmission, wherein
the data processing unit is configured to process the data provided by the gas measuring device and/or by the central memory based on the system time and the gas measuring device time.

2. A system in accordance with claim 1, wherein the interface and the data identification unit are integrated in a gateway.

3. A system in accordance with claim 1, wherein the interface is configured to transmit information on a performed establishment of a connection to the gas measuring device during the establishment of a data connection between the gas measuring device and the interface.

4. A system in accordance with claim 3, wherein the gas measuring device is configured to store the information on the performed establishment of the connection with the interface in the memory of the gas measuring device and to store information on a performed severing of the connection with the interface at the time of the severing of the data connection between the gas measuring device and the interface in the memory of the gas measuring device.

5. A system in accordance with claim 1, further comprising a compensation unit configured to convert the detection time according to the gas measuring device time of the historical data into a detection time according to the system time based on the system time and the gas measuring device time during the data transmission and to assign the converted detection time to the respective data.

6. A system in accordance with claim 1, further comprising a compression unit configured to reduce a size and/or a quantity of the data provided by the gas measuring device as a function of at least one decision criterion.

7. A system in accordance with claim 6, wherein the compression unit is configured to delete data if the decision criterion is not met.

8. A system in accordance with claim 6, wherein the decision criterion takes into consideration at least one of a change in a measured value, which occurs during a time interval, an intensity of a change in a measured value and a number of data detected within a time period.

9. A system in accordance with claim 1, wherein the memory of the gas measuring device comprises memory areas, in which respective data concerning specific events are stored and the gas measuring device is configured such that the data stored in one of the memory areas can be transmitted separately from data stored in another of the memory areas.

10. A system in accordance with claim 1, further comprising another interface, wherein at least two interfaces are provided, and the gas measuring device is configured to select one of the at least two interfaces for the data transmission as a function of a transmission power necessary for the data transmission and/or of the signal quality of the data transmission.

11. A system in accordance with claim 1, wherein the memory of the gas measuring device is configured to store the data on a rolling basis.

12. A system in accordance with claim 1, wherein the gas measuring device further comprises a control unit configured to establish a connection to the interface for transmitting the data stored in the memory to the central data processing unit, based on a decision criterion.

13. A system in accordance with claim 1, wherein the data processing unit is configured to determine, from the detected data, a concentration of at least one gas, a number of alarms or measuring errors and/or forces that acted on the gas measuring device during a past time period.

14. A system in accordance with claim 13, wherein the gas measuring device comprises an output unit configured to provide an output based on the determination of the data processing unit.

15. A mobile gas measuring device for a system for analyzing data, which system comprises: the mobile gas measuring device; a data processing unit; an interface configured to receive the current and/or historical data from the gas measuring device and to feed the received data to the data processing unit or to a central memory; and a data identification unit, associated with the data processing unit and/or the central memory, and configured to add a specific identifier to the data provided by the gas measuring device, the data identification unit being further configured to add, to the data provided by the gas measuring device, information on a system time during the data transmission and on a gas measuring device time during the data transmission, wherein the data processing unit is configured to process the data provided by the gas measuring device and/or by the central memory based on the system time and the gas measuring device time, the mobile gas measuring device comprising:
 a sensor means to detect data; and
 a measuring device memory, wherein
 the gas measuring device is configured to provide current data and/or historical data which are stored in the measuring device memory and contain information on the gas measuring device time at the time of a detection of the data, and to wire or wirelessly transmit the data to the interface, wherein the measuring device memory is configured to store the data on a rolling basis.

16. A mobile gas measuring device in accordance with claim 15, wherein the measuring device memory comprises memory areas, which can be connected separately or together to the interface for transmitting data to the data processing unit.

17. A mobile gas measuring device in accordance with claim 15, further comprising a control unit configured to establish a connection to the interface for transmitting the data stored in the memory to the central data processing unit, based on a decision criterion.

18. A data processing unit for a system for analyzing data, which system comprises the data processing unit; a gas measuring device configured to provide current data and/or historical data which are stored in a memory of the gas measuring device and contain information on the gas measuring device time at the time of a detection of the data, and to wired or wirelessly transmit the data; an interface configured to receive the current and/or historical data from the gas measuring device and to feed the received data to the data processing unit or to a central memory; and a data identification unit, associated with the data processing unit and/or the central memory, and configured to add a specific identifier to the data provided by the gas measuring device, the data identification unit being further configured to add, to the data provided by the gas measuring device, information on a system time during the data transmission and on a gas measuring device time during the data transmission, wherein:
 the data processing unit is configured to process the data provided by the gas measuring device and/or by the central memory based on the system time and the gas measuring device time; and
 the data processing unit is configured to determine, from the detected data, a concentration of at least one gas, a number of alarms or measuring errors and/or forces that acted on the gas measuring device during a past time period and to output them via an output unit.

* * * * *